United States Patent
Sanicola et al.

(10) Patent No.: US 11,759,281 B2
(45) Date of Patent: Sep. 19, 2023

(54) SYSTEMS AND METHODS FOR DEEP BRAIN STIMULATION SURGERY

(71) Applicants: Henry Sanicola, Hidden Hills, CA (US); Brody Stewart, Dahinda, IL (US); Caleb Stewart, Dahinda, IL (US)

(72) Inventors: Henry Sanicola, Hidden Hills, CA (US); Brody Stewart, Dahinda, IL (US); Caleb Stewart, Dahinda, IL (US)

( * ) Notice: Subject to any disclaimer, the term of this patent is extended or adjusted under 35 U.S.C. 154(b) by 0 days.

(21) Appl. No.: 16/979,095

(22) PCT Filed: Jul. 13, 2020

(86) PCT No.: PCT/US2020/041821
§ 371 (c)(1),
(2) Date: Sep. 8, 2020

(87) PCT Pub. No.: WO2022/015282
PCT Pub. Date: Jan. 20, 2022

(65) Prior Publication Data
US 2023/0094642 A1   Mar. 30, 2023

(51) Int. Cl.
*A61B 90/10* (2016.01)

(52) U.S. Cl.
CPC .................. *A61B 90/10* (2016.02)

(58) Field of Classification Search
CPC .......... A61B 90/10; B25B 5/06; B25B 5/067; B25B 5/068; B25B 5/08; B25B 5/082; B25B 5/10; B25B 5/101; B25B 5/102; B25B 5/103; B25B 5/104; B25B 23/0007; B25B 23/0021; E05B 1/00; E05B 1/0053; F16D 1/076; F16D 1/08; F16D 1/0829; F16D 1/0847; F16D 1/0852; F16D 1/0864; F16D 1/101; F16L 23/06; F16L 23/08; F16L 23/10
See application file for complete search history.

(56) References Cited

U.S. PATENT DOCUMENTS

| | | | |
|---|---|---|---|
| 6,672,631 | B1 | 1/2004 | Weinhold |
| 2002/0088087 | A1 | 7/2002 | Keith |

FOREIGN PATENT DOCUMENTS

| | | | | |
|---|---|---|---|---|
| JP | 2014/018947 | A | 2/2014 | |
| JP | 2014018947 | * | 2/2014 | ............. B25B 33/00 |
| WO | WO-03/039386 | A1 | 5/2003 | |

OTHER PUBLICATIONS

International Search Report and Written Opinion for PCT/US2020/041821, dated Sep. 25, 2020, 10 pgs.
International Preliminary Report on Patentability and Written Opinion for PCT/US2020/041821, dated Jan. 23, 2023, 9 pgs.

* cited by examiner

*Primary Examiner* — Robert A Lynch
(74) *Attorney, Agent, or Firm* — Philip L. Bateman (57) ABSTRACT

Systems and methods for operating deep brain stimulation are disclosed. In certain embodiments, the systems and methods encompass an adapter a body portion, a shank portion; and a cam system. The cam system is comprised of a camshaft and an eyebolt that secures a latch. The body portion of the adapter is coupled to a hand knob of a microdriver and the shank portion is coupled to a drill. When the drill is activated, the adapter transmits rotational energy from the drill to the hand knob of the microdriver, which automates the raising and lowering of its needle.

14 Claims, 7 Drawing Sheets

SYSTEMS AND METHODS FOR DEEP BRAIN STIMULATION SURGERY

RELATED APPLICATIONS

The present application is a U.S. National Stage of International Application No. PCT/US20/41821, filed Jul. 13, 2020. The entire contents of this application is incorporated by reference.

FIELD OF THE INVENTION

The present invention relates to systems and methods for deep brain stimulation. The invention may be applied in such fields as neurosurgery for the treatment of movement disorders.

BACKGROUND OF THE INVENTION

Deep brain stimulation involves the implantation of electrodes into deep structures of the brain near the globus pallidum, subthalamic nucleus, and red nucleus. The electrodes stimulate the motor circuits of the brain to improve motor function.

Accurate implantation of electrodes requires surgical planning and neuronavigation. The surgical planning involves techniques for surgical treatment or scientific investigation that permit the accurate positioning of probes inside the brain or other parts of the body, based on three-dimensional diagrams. Neuronavigation involves the use of a camera system and fiducials on the patient to register MRI/CT scans to patient for surgical precision.

There are two commonly practiced techniques for deep brain stimulation that utilize a stereotactic frame and a frameless stereotactic system. A stereotactic frame is a metal device fitted over the head of a patient about to undergo brain surgery. It creates a three-coordinate reference system for precise surgical intervention independent of patient movement between the planning phase and the actual operation. A frameless stereotactic system, such as the Nexframe system produced by Medtronic, is comprised of tower that connects to the base that is attached to a skull with screws. These systems provide different mounting mechanisms for the microelectrode drive to be attached. The frame and microdriver are localized in the correct position and trajectory using fiducials and guidance probes in neuronavigation.

The microelectrode recording needle is inserted into the microdriver to determine the final target for the electrode. Both frame and frameless stereotactic systems for multiple medical device companies utilize a knob for raising and lowering the recording needle and microelectrode into and out of the brain. The knob on the microdriver is manually turned for fine control of needle and electrode descent. Automated microdrivers exist but these machines are much more expensive and not commonly used.

As such, there is a need in the art for a device that allows surgeons to remove recording needles more rapidly and reduce the time of surgery without paying the upgrade costs for an automated microdriver.

SUMMARY OF THE INVENTION

This invention provides systems and methods to utilize a disposable, sterile battery powered driver as a power attachment for a microdriver. In certain embodiments, the invention functions as an adapter between the two devices; it connects the drive output of the electric rotary drill to the hand knob of a microdriver. The electric rotary driver has the ability to rotate the knob more quickly than if it were to be rotated by hand and therefore can increase the rate of removing or lowering the recording needle. The manipulation of the needle often may occur several times during a procedure and thus the device significantly decreases the overall time of the procedure.

In certain embodiments, the components of the cam system are comprised of the bit, eyebolt, latch, and the pin. The adapter's shank connects to the disposable driver. The shank can be modified to fit a number of battery drivers/drills, while the body can attach to different microdriver knobs produced by device companies. The adapter functions by connecting the drill to the microdriver knob, which protrudes from the body of the microdriver.

DETAILED DESCRIPTION OF PREFERRED EMBODIMENTS

A more complete appreciation of the invention and many of the attendant advantages thereof will be readily obtained as the same becomes better understood by reference to the following detailed description when considered in connection with the accompanying drawings, wherein.

DETAILED DESCRIPTION OF PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. Several preferred embodiments of the invention are described for illustrative purposes, it being understood that the invention may be embodied in other forms not specifically shown in the drawings.

Figure 1:
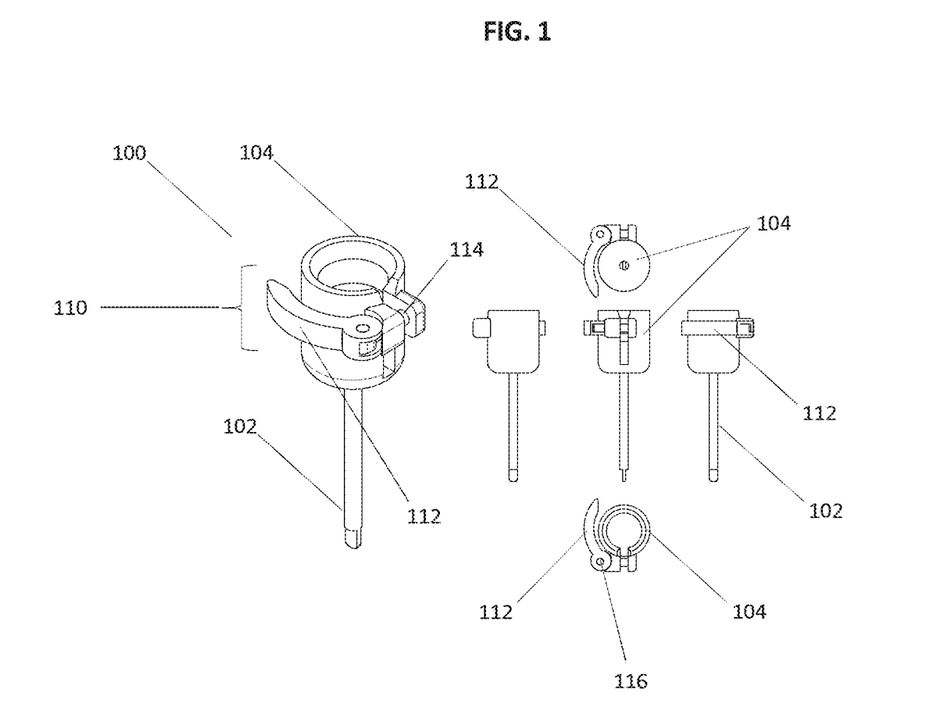
FIG. 1 is an exemplary embodiment of the adapter and assembly of the invention, in top-down and side views.
Figure 2:
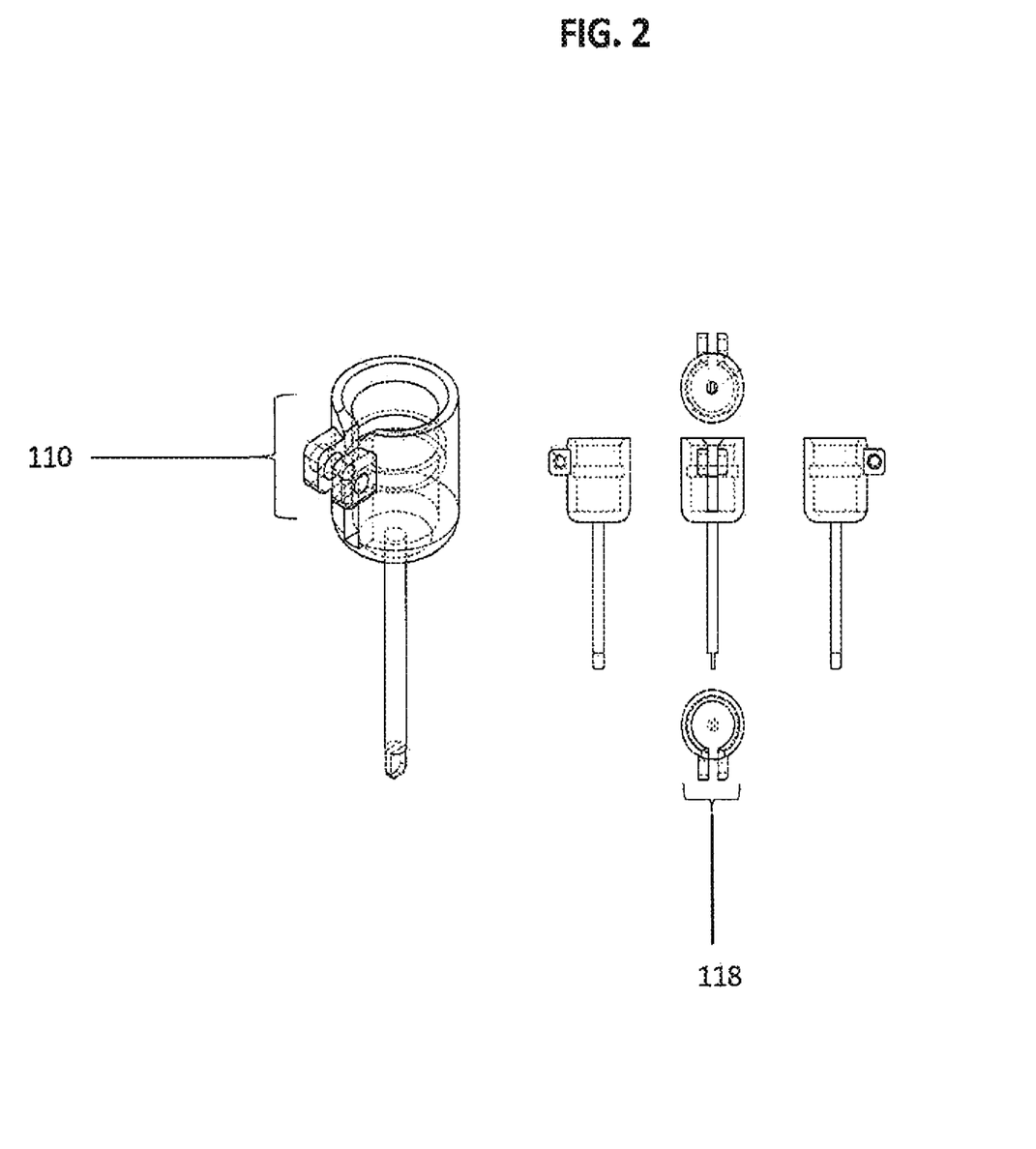
FIG. 2 is an exemplary embodiment of the body and shank portions of the invention, in top-down and side views.
Figure 4:
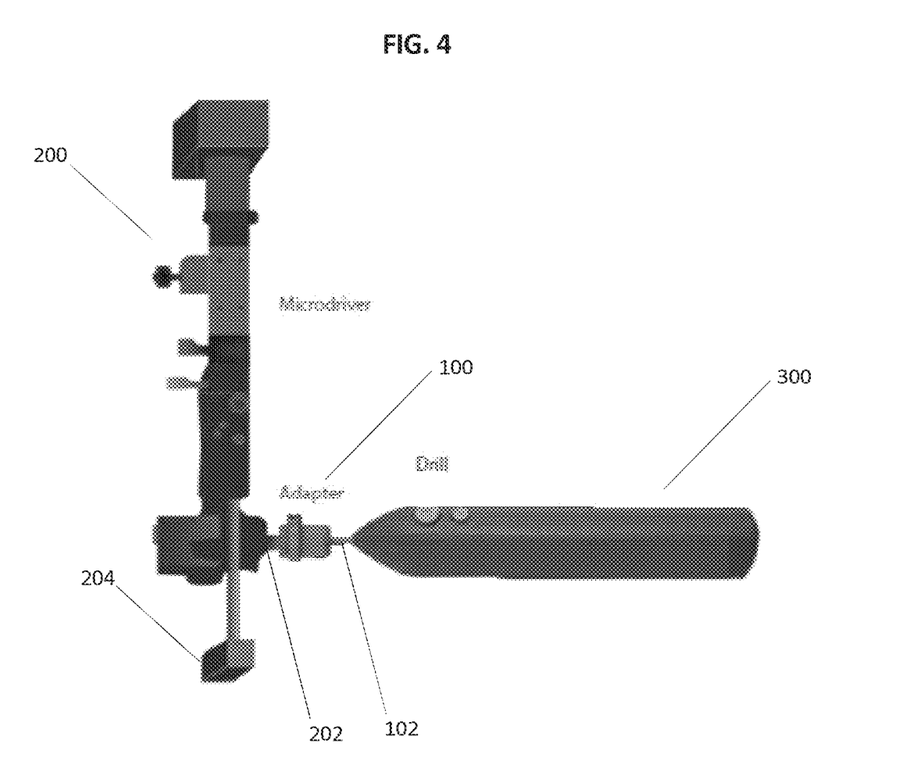
FIG. 4 is an exemplary embodiment of the invention, as assembled.

FIG. 1 is an exemplary embodiment of the adapter 100 and assembly of the invention, in top-down and side views. Referring momentarily to FIG. 4, the adapter 100 is situated between the microdriver 200 and the drill 300. The adapter 100 is configured to mate the drill 300 to the microdriver 200. As shown in FIG. 1, the adapter 100 is comprised of a shank portion 102, a body portion 104, and a clamp or cam system 110. As shown in FIGS. 1 and 2, the cam system 110 is further comprised of a camshaft 112, an eyebolt 114, a pin 116, and a latch 118.

As shown in FIG, 2, the shank portion 102 of the adapter is preferably an elongated cylindrical protrusion from the body portion 104. The body portion 104 is also preferable cylindrical and greater in diameter than the shank portion 102. The body portion 104 is cup-shaped and hollow at the end that is distal to the shank portion 102. Thus, the body portion 104 has an outer portion with a bottom portion at a proximal end so that the proximal end is closed and coupled with the shank portion 102, which extends outward therefrom. The body portion 104 has a top at a distal end that is open to permit access to the hollow interior space. The hollow interior space of the body portion 104 is configured to receive and mate with the microdriver knob 202 of the microdrive 200, as explained in greater detail below. The shank portion 102 is configured to mate with the bottom portion of the body portion 104. In certain embodiments, the shank portion 102 is mated to substantially the center of the bottom portion of the body portion 104. The opposite end of the shank portion 102 is configured to mate with the drill 300, as will be explained in greater detail below. The shank portion 102 can be modified to fit a number of battery drivers or drills The shank portion 102 can be adapted to the drill 300 being used by changing the conformation of the shank portion 102, for example, by changing the shank portion 102 to square type terminus (Robertson-type connection) or changing the diameter of the substantially circular end-piece of the shank portion 102. Hexagonal or octagonal drill bits may also be attached to the end-piece of the shank portion 102. The body portion 104 can similarly be modified to fit a number of different microdriver hand knobs 202 (see FIG. 4), as produced by device companies. The diameter of the body portion 104 can be up- or down-scaled. The body portion 104 may be exemplarily oversized in diameter and come with a variety of sleeves that can be placed inside the body portion 104 to adapt the body portion 104 to variable diameters. The sleeves may be color-coded to identify the diameter to which they are suited and to allow for easy, quick use by a surgical team.

As shown in FIGS. 1 and 2, the cam system 110 is mated to the adapter 100 and is comprised of a camshaft 112, an eyebolt 114, a pin 116, and a latch 118. The cam system 110 functions to allow for disconnection or reconnection to the microdriver knob 202 and provides a latching mechanism between microdriver 200 and the adapter 100.

Figure 3A:
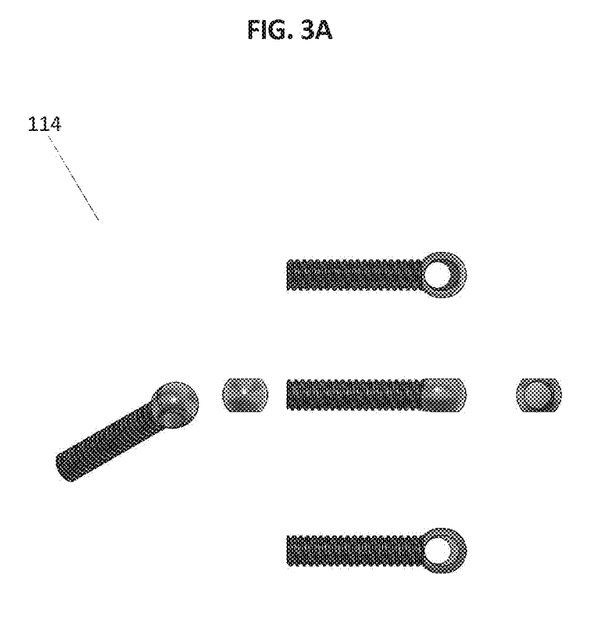
FIG. 3A is an exemplary embodiment of the eyebolt component of the invention, in top-down and side views.

FIGS. 3A through 3D show the various components of the cam system 110. FIG. 3A is an exemplary embodiment of the eyebolt 114 component of the invention, in top-down and side views. The body portion 104 has a vertical slit 120 that extends the entire length of the wall of the body portion 104 from the top to the bottom so that the body wall is open (i.e., disconnected and separated by a distance) at the slit 120. The latch 118 is a tab that extends orthogonally outward from the body portion 104 at each side of the slit 120. The eyebolt 114 has a threaded portion and a rounded head with a through-hole. The threaded portion of the eyebolt 114 extends across the slit 120 and passes through the two latches 118 to secure the cam system 110 to the body portion 104 of the adapter 100, as well as to secure the body portion 104 of the adapter to the hand knob 202 of the microdriver 200. The cam system 110 reduces the diameter of the hollow interior space of the body portion 104 as it moves between a locked or clamped position, where the body portion 104 has a reduced diameter, and an unlocked or release position, where the body portion 104 has a larger diameter. Thus, the clamp or cam system 110 operates as a quick release for removing and replacing the hand knob 202 of the microdriver 200, which is configured to mate with the interior hollow space of the body portion 104.

Figure 3B:
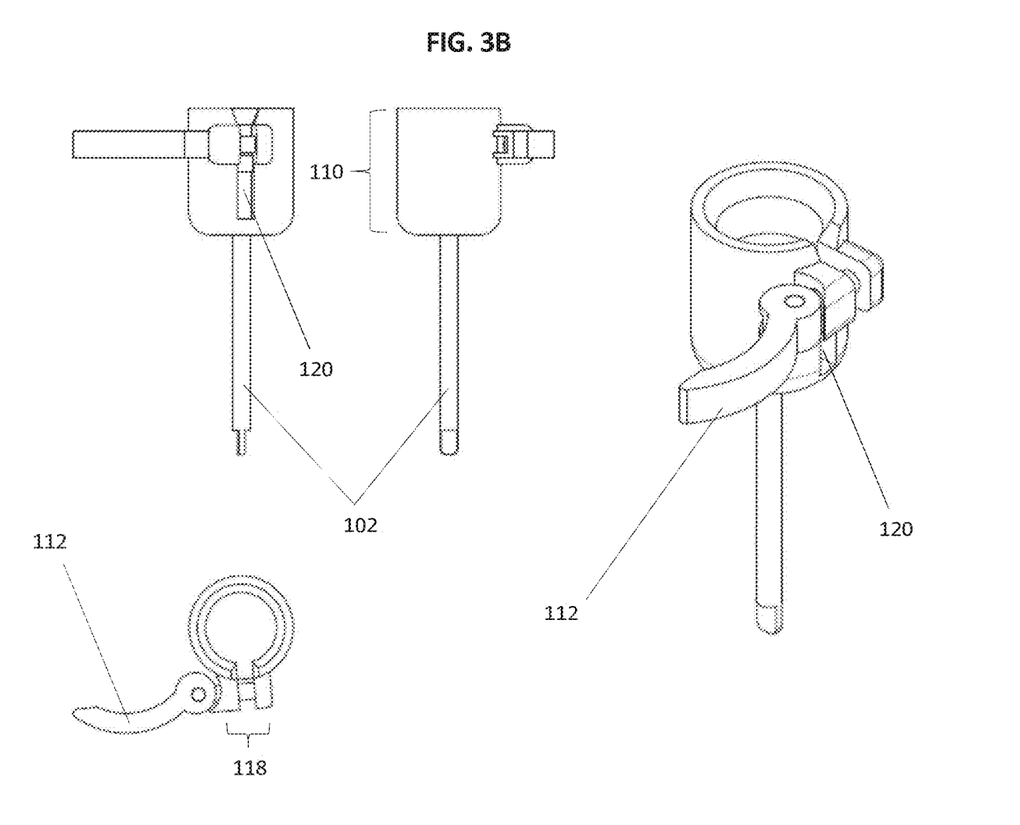
FIG. 3B is an exemplary embodiment of the cam component of the invention in an open configuration, in top-down and side views.

FIG. 3B is an exemplary embodiment of the cam system 110 of the invention in an open configuration, in top-down and side views. The camshaft 112 is an elongated member that extends from the cam system 110. The elongated portion of the camshaft 112 is preferably curved so that it wraps around a part of the body portion 104 of the adapter to form a handle. In certain embodiments, there is a rounded portion of the camshaft with a through hole. A pin 116 passes through the camshaft through hole and through the through hole in the eyebolt 114 to secure the camshaft 112 to the eyebolt 114. The threaded portion of the eyebolt 114 passes through a central bore in the latches 118. The eyebolt 114 is secured by a fastener such as a nut, at the opposite side of the latches 118.

Figure 3C:
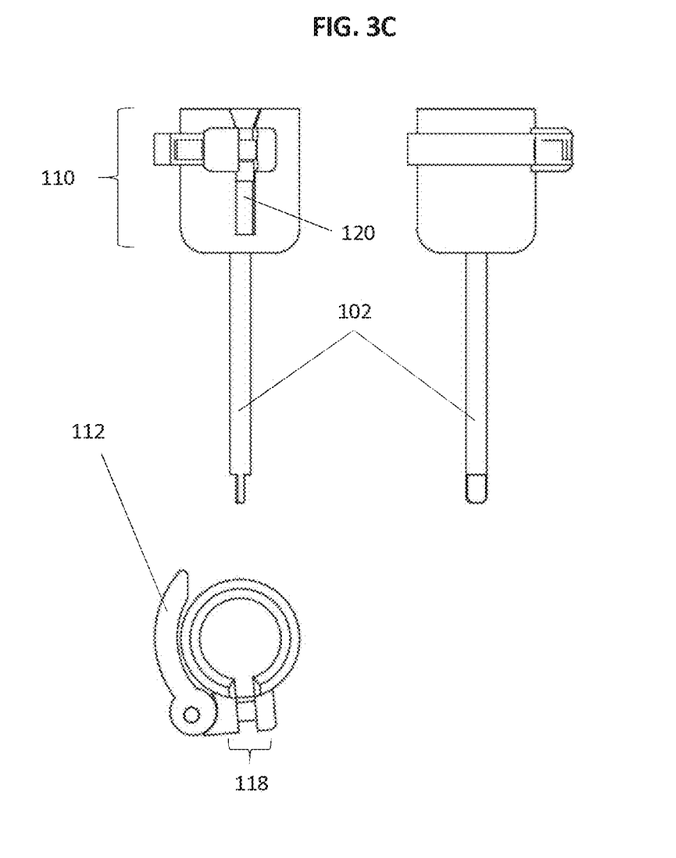
FIG. 3C is an exemplary embodiment of the cam component of the invention in a closed configuration, in top-down and side views.

The base of the handle is circular and has a thicker portion on one side of the pin 116 and a thinner portion on the other side of the pin 116. In the open position, the thinner portion is aligned with the latch 118 and disengages from the latch 118. In the closed position, the thicker portion is aligned with the latch 118 and engages the latch 118, pulling the latches 118 together and narrowing the slit 120. The wall of the body portion 104 of the adapter is substantially rigid so that the slit 120 is biased to the opened position, but somewhat flexible so that the slit 120 comes together in the closed position, as shown in FIG. 3C. In one embodiment, the slit 120 only partially comes together and the sides of the slit 120 do not contact one another, though in other embodiments the sides can touch.

In operation, the user pulls outward on the camshaft 112, which moves the cam system 110 to the unlocked or open position, whereby the body can separate outward at the slit 120 to allow the body 104 to extend outward and have a larger diameter. The hand knob 202 can then be received in the widened diameter of the hollow interior. Once the hand knob 202 is positioned within the hollow interior, the user then moves the camshaft 122 inward against the side of the body portion 104 (as shown in FIG. 1) into the locked or closed position, as shown in FIG. 3C, whereby the operation of the camshaft 112 against the curved distal surface of the latch 118 pulls the latches 118 together thereby narrowing the slit 120 and the diameter of the body 104. In the locked position, the hand knob 202 is clamped or locked to the body portion 104 of the adapter 100. The shank portion 102 can then be placed in the drill 300 and locked thereto by features of the drill 300. The drill 300 can then be operated to rotate the adapter 100 and hand knob 202.

The camshaft 112 functions to transmit the rotation energy from the drill 300 to the hand knob 202 of the microdriver. That is, the shank 102 is fixedly coupled to the drill 300 and to the adapter. The drill 300 rotates the shank 102, which in turn rotates the entire adapter 100. As the adapter 100 rotates, the body portion 104 rotates. When the hand knob 202 is lockably engaged with the body portion 104, the body portion 104 in turn rotates the hand knob 202. The camshaft 112 preferably latches on to the microdriver 200, but does not power the microdriver 200. The power comes from the drill 300. The camshaft 112 allows for quick disconnection and reconnection and acts as a latching mechanism that provides secure coupling to the microdriver 200.

Figure 3D:
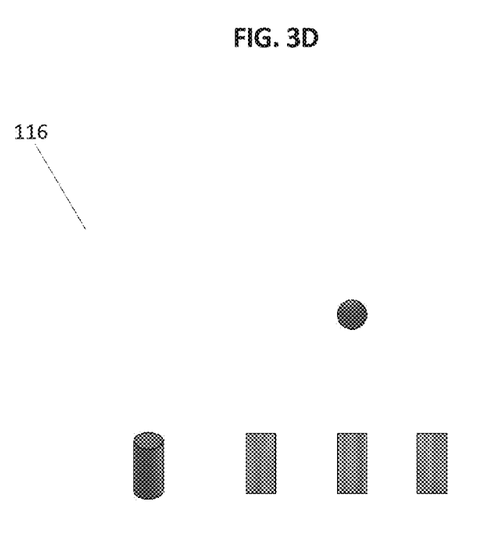
FIG. 3D is an exemplary embodiment of the pin component of the invention, in top-down and side views.

FIG. 3D is an exemplary embodiment of the pin 116 component of the invention, in top-down and side views. In certain embodiments, the pin 116 is used to mate the camshaft 112 to the cam system.

FIG. 4 shows an assembled embodiment of the invention. The microdriver 200 is comprised of the hand knob 202 and the needle mount 204. Typically, the hand knob 202 would be used to raise and lower the needle in the course of surgery. Instead, the body portion 104 of the adapter 100 is mated to the hand knob 202 of the microdriver. On the other side, the shank portion 102 of the adapter 100 is mated to the drill 300. The adapter 100 thus allows the drill 300 to supply power to the microdriver 200 such that the hand knob 202 need not be manually turned. The drill 300 thus has the ability to rotate the hand knob 202 more quickly than if it were to be rotated by hand and therefore can increase the rate of removing or lowering the needle that is mated to the needle mount 204.

In typical implementations of the invention, the adapter 100 is configured to be situated between the microdriver 200 and the drill 300 during deep brain stimulation procedures, such as those that involve the implantation of electrodes into deep structures of the brain. In such procedures, a microelectrode recording needle is inserted into the needle mount 204 to determine the final target for the electrode. The microdriver 200 has a hand knob 202 that must be turned manually by the operator in order to raise and lower the needle that is inserted into the needle mount 202. The hand knob 202 allows for fine control of needle and electrode descent. When the adapter 100 is mated to the hand knob 202 of the microdriver 200 and the drill, however, the hand knob 202 does not require manual operation, which can slow and complicate the procedure.

Instead, when the drill 300 is activated, the adapter 100 transfers its rotational energy to the hand knob 202, which in turn raises and lowers the needle inserted into the needle mount 204. In that manner, the operation of the microdriver 200 is automated. Furthermore, since the adapter 100 can accept a variety of hand knob 202 sizes and drill 300 sizes, a single adapter 100 can be used for a variety of procedures, regardless of microdriver 200 and drill 300 size.

It is further noted that the description and claims use several geometric or relational terms, such as curved, elongated, cylindrical. In addition, the description and claims use several directional or positioning terms and the like, such as interior space, top, bottom, distal, and proximal. Those terms are merely for convenience to facilitate the description based on the embodiments shown in the figures, and are not intended to limit the disclosure. Thus, it should be recognized that the disclosure can be described in other ways without those geometric, relational, directional or positioning terms. In addition, the geometric or relational terms may not be exact. And, other suitable geometries and relationships can be provided without departing from the spirit and scope of the disclosure.

The foregoing description and drawings should be considered as illustrative only of the principles of the invention. The invention is not intended to be limited by the preferred embodiment and may be implemented in a variety of ways that will be clear to one of ordinary skill in the art. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. An adapter comprised of:
   (a) a body portion having a bottom, an open top, an interior space, and an outer portion, the interior space configured to receive a hand knob of a microdriver;
   (b) a shank portion fixedly coupled to the bottom at the outer portion of the body portion and extending outward from the bottom; and
   (c) a quick release mechanism comprised of a locking system having a handle and an eyebolt connected to a latch;
   wherein the quick release mechanism releasably locks the body portion to the hand knob of the microdriver and the shank portion is coupled to a drill; and wherein the adapter transmits rotational energy from the drill to the microdriver hand knob when the drill is operated.

2. The adapter of claim 1 wherein the handle attaches to the locking system at a pin.

3. The adapter of claim 1 wherein the body portion is configured to fit a plurality of microdriver hand knobs.

4. The adapter of claim 1 wherein the shank portion is configured to fit a plurality of drills.

5. The adapter of claim 1 wherein the body portion is substantially cylindrical.

6. The adapter of claim 1 wherein the rotational energy from the drill raises and lowers a needle coupled to the microdriver.

7. The adapter of claim 1 wherein the shank portion is mated to the bottom surface of the body portion.

8. A method of operating a microdriver comprising:
   (a) coupling a body portion of an adapter to a hand knob of a microdriver;
   (b) coupling a shank portion of the adapter to a drill; and
   (c) operating the drill to raise and lower a needle coupled to the microdriver, wherein the adapter transmits rotational energy from the drill to the microdriver hand knob.

9. The method of claim 8 wherein the body portion is coupled to a quick release mechanism comprised of a locking system having a handle and an eyebolt connected to a latch.

10. The method of claim 8 wherein the handle attaches to the locking system at a pin.

11. The method of claim 8 wherein the body portion is configured to fit a plurality of microdriver hand knobs.

12. The method of claim 8 wherein the shank portion is configured to fit a plurality of drills.

13. The method of claim 8 wherein the body portion is substantially cylindrical.

14. The method of claim 8 wherein the shank portion is mated to a bottom surface of the body portion.

* * * * *